(12) United States Patent
Pervez

(10) Patent No.: US 6,737,530 B2
(45) Date of Patent: May 18, 2004

(54) PROCESS

(75) Inventor: Mohammed Pervez, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/258,429

(22) PCT Filed: May 22, 2001

(86) PCT No.: PCT/SE01/01165

§ 371 (c)(1),
(2), (4) Date: Oct. 23, 2002

(87) PCT Pub. No.: WO01/90073

PCT Pub. Date: Nov. 29, 2001

(65) Prior Publication Data

US 2003/0166942 A1 Sep. 4, 2003

(30) Foreign Application Priority Data

May 24, 2000 (GB) .............................................. 0012448

(51) Int. Cl.$^7$ ............................................ C07D 211/70
(52) U.S. Cl. ....................................................... 546/342
(58) Field of Search ......................................... 546/342

(56) References Cited

U.S. PATENT DOCUMENTS 5,102,668 A 4/1992 Eichel et al.
6,300,330 B1 * 10/2001 Stocker et al. ......... 514/252.02

FOREIGN PATENT DOCUMENTS

| EP | 0 580 862 A1 | 2/1994 |
| EP | 0 717 988 A1 | 6/1996 |
| GB | 2 091 203 A | 7/1982 |
| WO | 98/21188 | 5/1998 |
| WO | 99/57113 | 11/1999 |
| WO | 01/47492 A1 | 7/2001 |

OTHER PUBLICATIONS

Gong, CA 133:207866, abstract of Synlett; vol (6), pp 829–831, 2000.*
Ennis, et al. Multikilogram–Scale Synthesis of a Biphenyl Carboxylic Acid Derivative Using a Pd/C–Mediated Suzuki Coupling Approach. Organic Process Research & Development, 3, 248–252 (1999).

Brown, et al. A Green, One–Pot Preparative Scale Route to the Biphenyldicarboxylic Acids, and the Synthesis and Thermomechanical Properties of Copolyesters Based on These Monomers. Polymer Preprints 41(1), 123–124 (2000).

Marck, et al. Aryl Couplings with Heterogeneous Palladium Catalysts: Tetrahedron Letters. 35(20), 3277–3280 (1994).

Martin, et al. Palladium–Catalyzed Cross–Coupling Reactions of Organoboronic Acids with Organic Electrophiles. Acta Chemica Scandinavica 47, 221–230 (1993).

Zhang, et al. Quinolone Antibacterials 1. 7-(2–Substituted–4–thiazolyl and thiazolidinyl)quilones. J. Heterocyclic Chem. 28, 673 (1991).

Bredereck, et al. Trisacylaminomethane: Synthesen und Umsetzungen. Chem. Ber. 96, 1505 (1963).

Ishikura, et al. A Novel Synthesis of 4–Aryl– and 4–Heteroarylpyridines via Diethyl(4–pyridyl) borane. Chem. Pharm. Bull., 33(11), 4755–4763 (1985).

Zoltewicz, et al. N–Methylation and N–Oxidation of the Less Reactive Nitrogen Atom of a 2,3'–Bipyridine. Two General Methods for Polyazines Tetrahedron, 51(11), 3103–3114 (1995).

Church, et al. New Synthetic Routes to 3–,5e, and 6–Aryl–2–chlorpyridines. J. Org. Chem. 60(12), 3750–3758 (1995).

Aoyagi, et al. Palladium–Catalyzed Cross–Coupling Reactions of Chloropyrazines with Aromatic Heterocycles. Heterocycles, 31(1), 257 (1992).

Sandosham, et al. Synthesis of Pyrimidinyl Triflates and Palladium–Catalyzed Coupling with Organotin and Organozinc Reagents. Heterocycles, 37(1), 501 (1994).

Wittenberger, et al. Dialkyltin Oxide Mediated Addition of Trimethylsilyl Azide to Nitriles: A Novel Preparation of 5–Substituted Tetrazoles. J. Org. Chem. 58, 4139–4141 (1993).

* cited by examiner

*Primary Examiner*—D. Margaret Seaman
(74) *Attorney, Agent, or Firm*—Ropes & Gray LLP

(57) ABSTRACT

A new process for the preparation of 4-(4-pyridinyl)benzoic acid, or a salt thereof.

11 Claims, No Drawings

PROCESS

CROSS-REFERENCE TO RELATED APPLICATIONS

This application is a national-stage filing under 35 U.S.C. 371 of PCT application PCT/SE01/01165, filed May 22, 2001, which claims priority from United Kingdom Application No. 0012448.7, filed May 24, 2000, the specifications of each of which are incorporated by reference herein. PCT Application PCT/SE01/01165 was published under PCT Article 21(2) in English.

FIELD OF THE INVENTION

The invention relates to a new process for the preparation of 4-(4-pyridinyl)benzoic acid, or a salt thereof.

BACKGROUND 4-(4-Pyridinyl)benzoic acid, sodium salt (CAS registry number 207798-97-8), is useful as an intermediate in the synthesis of 1-(6-chloronaphth-2-ylsulphonyl)-4-[4-(4-pyridyl)benzoyl]piperazine disclosed as Example 7 in PCT publication WO9821188. A number of references describe the preparation of 4-(4-pyridinyl)benzoic acid. For example, a process is described in WO9821188, Example 4, where the intermediate is made using a three stage process involving a palladium-mediated biaryl Suzuki coupling as the key step as shown in Scheme 1.

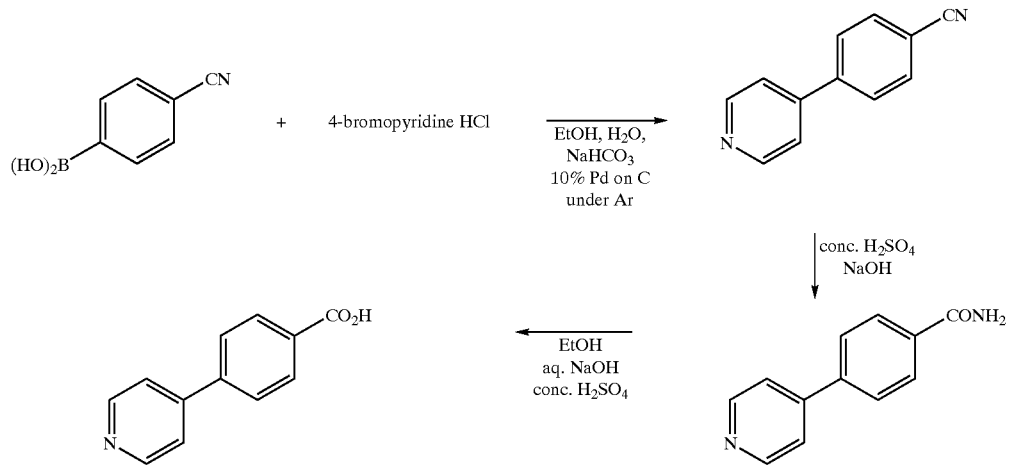

Scheme 1

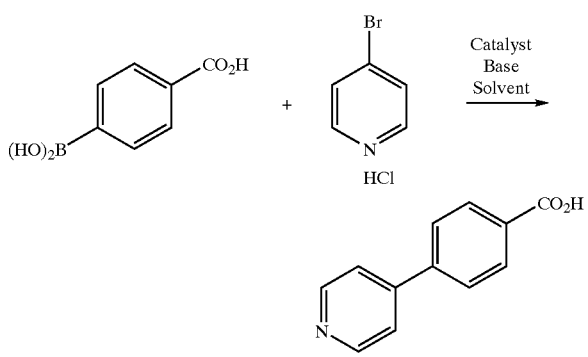

Scheme 2

Therefore, in a first aspect the invention is a process for the preparation of 4-(4-pyridinyl)benzoic acid, or a salt thereof, comprising reacting a mixture of 4-carboxybenzeneboronic acid, optionally in the form of a salt, and 4-bromopyridine, also optionally in the form of a salt, particularly the hydrochloride salt, in the presence of base and a catalyst, all reactants being substantially dissolved in a solvent.

To carry out the reaction, the mixture may be heated. Particularly, the mixture may be heated to reflux.

DESCRIPTION OF THE INVENTION

We have surprisingly found that 4-carboxybenzeneboronic acid and 4-bromopyridine hydrochloride may be directly coupled together, in high yield, without the need to protect the carboxylic acid functionality, as shown in Scheme 2.

Catalysts suitable for use in the process are, for example, Ni and particularly, Pd(0) or Pd(II) based catalysts. Specific and preferred catalysts are those described herein.

Bases suitable for the use in the invented process may be weak or strong and are advantageously selected on the basis of being soluble in the solvent used. Certain strong bases may be less suitable as they may promote proto-deboronation of the boronic acid. The presence of this adverse reaction may be determined simply by detecting the formation of benzoic acid, such as, for example by the use of HPLC. The nature of the proto-deboronation reaction, and how to avoid it, are described in Thomas I. Wallow and Bruce M. Novak J. Org. Chem. 1994, 59, 5034–5037, and references cited therein. Specific and preferred bases are described herein.

Solvents suitable for use in the reaction are selected for an ability to solubilise the intermediates and the base. Suitable solvents include aqueous and organic solvents, or mixtures of either or both. Particular solvents are aqueous, protic and dipolar aprotic solvents or mixtures thereof Specific and preferred solvents are described herein.

It has been found that using the process of the Invention, 4,4'-biphenyldicarboxylic acid (CAS registry number 787-70-2) of Formula I, a homo-coupled impurity of the 4-carboxybenzeneboronic acid intermediate may be formed.

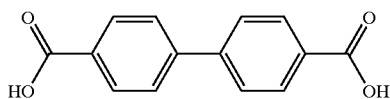

Formula I

Once present, this impurity is difficult to reduce to levels acceptable for the manufacture of pharmaceuticals. However, the yield of 4-(4-pyridinyl)benzoic acid has been improved and the level of the homo-coupled impurity reduced by using an appropriate catalyst, base and solvent system in the invented process.

Accordingly, a second aspect of the invention is a process that can be scaled up for large scale manufacture of 4-(4-pyridinyl)benzoic acid in a yield of 90% (w/w) or more whilst controlling the level of the homo-coupled impurity to less than 2% (w/w), and usually less than 0.5% (w/w).

This aspect of the Invention is a process for the preparation of 4-(4-pyridinyl)benzoic acid, or a salt thereof, comprising reacting 4-carboxybenzoic acid, optionally in the form of a salt, with 4-bromopyridine, optionally in the form of a salt, and with a base all reactants being dissolved in a solvent, particularly aqueous ethanol, and in the presence of catalyst $(R_3P)_4Pd$ catalyst, wherein R is an aromatic or heteroaromatic ring, cyclic alkyl or aliphatic group. Particularly R is phenyl.

This process provides material of acceptable organic purity for use in the manufacture of pharmaceuticals. However, the level of residual palladium catalyst may be high, for example greater than 500 ppm, according to pharmaceutical standards. Accordingly, a number of different process modifications were investigated to reduce the amount of catalyst residue in the isolated material. Such modifications included ligand exchange, base treatment, adsorption onto solid supports and liquid-liquid extraction. Of these liquid-liquid extraction showed the most promise on a small scale but was found to be unreliable on scale-up.

An alternative approach to minimising the catalyst residue was therefore investigated. This involved the use of a water soluble palladium catalyst. Examples of such catalysts are described in the literature. For example, Christian Amatore, Errol Blart, Jean Pierre Genet, Anny Jutand, Sandrine Lemaire-Adoire, and Monique Savignac. J. Org. Chem. 1995, 60, 6829–6839, describe the preparation from palladium acetate and the trisodium salt of 3,3',3"-phosphinidyne-tris(benzenesulphonic acid).

Therefore, a third aspect of the Invention is a process for the manufacture of 4-(4-pyridinyl)benzoic acid, or a salt thereof, comprising reacting 4-carboxybenzeneboronic acid, optionally in the form of a salt, with 4-bromopyridine, optionally in the form of a salt, and with a base all parts being substantially dissolved in a solvent and in the presence of a water soluble Pd(0) based catalyst.

Particularly, in this aspect of the Invention the Pd(0) catalyst is formed in situ, by mixing a Pd(U)species, such as palladium acetate, with a ligand, such as 3,3',3"-phosphinidyne-tris(benzenesulphonic acid)trisodium salt, in a suitable solvent.

The following non-limiting examples illustrate the invention.

EXAMPLE 1

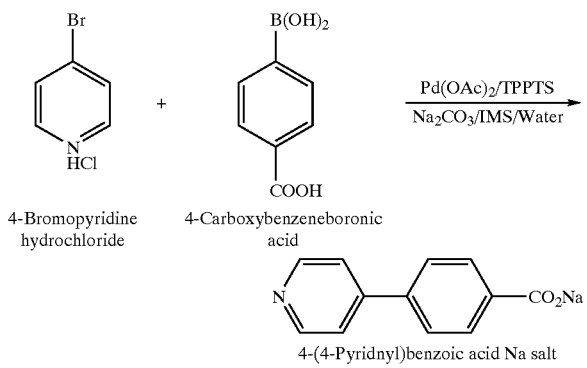

4-Bromopyridine hydrochloride

4-Carboxybenzeneboronic acid 4-(4-Pyridnyl)benzoic acid Na salt

To a slurry of 4-carboxybenzeneboronic acid (100.0 g at 95% strength, 0.572 moles, 1.00 mol. eq.), 4-bromopyridine hydrochloride (114.7 g at 99% strength, 0.584 moles, 1.02 mol. eq.) and palladium acetate (0.262 g at 98% strength, 0.001145 moles, 0.002 mol. eq.) in a mixture of water (665 mL, 7.0 volumes) and Industrial grade Methylated Spirits (IMS) (475 mL, 5.0 volumes) was added dropwise a solution of $Na_2CO_3$ (151.7 g at 100% strength, 1.431 moles, 2.50 mol. eq.) in water (1140 mL, 5.0 volumes). 3,3',3"-phosphinidyne-tris(benzenesulphonic acid) trisodium salt (TPPTS) (6.51 g, at 30% w/w solution in water, 0.003436 mole, 0.006 mol. eq.) was then added. The mixture was refluxed (Ca. 84° C.) for 5 hours under an inert atmosphere of nitrogen. After Cooling to ambient temperature (20° C.) the product was isolated by filtration and dried to a constant weight to give the title compound in 91% yield.

EXAMPLE 2

To a suspension of 4-carboxybenzeneboronic acid (4-CBBA, 1.00 mol. eq.), 4-bromopyridine hydrochloride (1.00 mol. eq.) and tetrakis(triphenylphosphine)palladium (0) (0.0075 mol. eq.) in IMS (14.0 volumes) was added a solution of potassium carbonate (2.50 mol. eq.) in water (14.0 volumes) and the mixture refluxed for 16 hours. The mixture was filtered and the filtrate extracted three times with toluene. IMS (9.1 volumes) was then distilled away and replaced with acetonitrile (10.6 volumes) before neutralisation with glacial acetic acid (2.6 volumes). The product was filtered, washed with water (6.0 volumes) followed by acetone (11.3 volumes) and then dried.

What is claimed is:

1. A process for the preparation of 4-(4-pyridinyl)benzoic acid, or a salt thereof, said process comprising: reacting a mixture of 4-carboxybenzeneboronic acid, optionally in the form of a salt, 4-bromopyridine, also optionally in the form of a salt, and a base, all parts being substantially dissolved in a solvent, in the presence of a catalyst.

2. The process of claim 1 wherein said mixture is heated.

3. The process of claim 1 wherein said catalyst is $(R_3P)_4Pd$, wherein R is selected from an aromatic ring, a heteroaromatic ring, a cycloalkyl group or an aliphatic group.

4. The process of claim 2 wherein said catalyst is $(R_3P)_4Pd$, wherein R is selected from an aromatic ring, a heteroaromatic ring, a cycloalkyl group or an aliphatic group.

5. The process of claim 3 wherein said aromatic ring is phenyl.

6. The process of claim 4 wherein said aromatic ring is phenyl.

7. The process of claim 1 wherein said catalyst is a water soluble Pd(0) catalyst.

8. The process of claim 1 wherein said base is potassium carbonate or sodium carbonate.

9. The process of claim 2 wherein said base is potassium carbonate or sodium carbonate.

10. The process of claim 1 wherein said solvent is mixture of water and an organic solvent.

11. The process of claim 2 wherein said solvent is mixture of water and an organic solvent.

* * * * *